(12) United States Patent
Ahmad (10) Patent No.: US 6,491,718 B1
(45) Date of Patent: Dec. 10, 2002

(54) INTRA VASCULAR STENT

(76) Inventor: Amjad Ahmad, 3967 Donegal Way, Eagan, MN (US) 55112

(*) Notice: Subject to any disclaimer, the term of this patent is extended or adjusted under 35 U.S.C. 154(b) by 48 days.

(21) Appl. No.: 09/678,049

(22) Filed: Oct. 3, 2000

Related U.S. Application Data (60) Provisional application No. 60/157,822, filed on Oct. 5, 1999.

(51) Int. Cl.$^7$ .................................................. A61F 2/06
(52) U.S. Cl. ..................................................... 623/1.15
(58) Field of Search ...................... 623/1.15, 1.11–1.14, 623/1.16, 1.17, 1.18, 1.2, 1.21, 1.22, 1.23, 900, 901

(56) References Cited

U.S. PATENT DOCUMENTS

| | | |
|---|---|---|
| 4,655,771 A | 4/1987 | Wallsten |
| 5,645,559 A | 7/1997 | Hachtman et al. |
| 5,695,516 A | 12/1997 | Fischell et al. |
| 5,697,971 A * | 12/1997 | Fischell et al. ............ 623/1.15 |
| 5,749,919 A | 5/1998 | Blanc |
| 5,860,999 A | 1/1999 | Schnepp-Pesch et al. |
| 5,861,027 A | 1/1999 | Trapp |
| 5,895,406 A | 4/1999 | Gray et al. |
| 5,911,754 A | 6/1999 | Kanesaka |
| 5,913,895 A | 6/1999 | Burpee et al. |
| 5,913,897 A * | 6/1999 | Corso, Jr. et al. .......... 623/1.15 |
| 5,931,867 A | 8/1999 | Haindl |
| 5,935,162 A | 8/1999 | Dang |
| 5,938,682 A | 8/1999 | Hojeibane et al. |
| 5,968,093 A | 10/1999 | Kranz |
| 5,980,553 A | 11/1999 | Gray et al. |
| 6,068,656 A | 5/2000 | Von Oepen |
| 6,264,685 B1 * | 7/2001 | Ahari ........................ 623/1.15 |

FOREIGN PATENT DOCUMENTS

| | | | |
|---|---|---|---|
| JP | 10-52503 | * 2/1998 | ................ 623/1.15 |
| WO | 99/17680 | * 4/1999 | ................ 623/1.15 |

* cited by examiner

Primary Examiner—Michael J. Milano
Assistant Examiner—Jackie Tan-Uyen T. Ho
(74) Attorney, Agent, or Firm—Janet Peyton Schafer (57) ABSTRACT

A radially expandible intra vascular stent 20 is provided with improved radially expandible strength due to increased amounts of metal surface area while flexibility is increased due to the unique stent wall surface pattern. In the un-expanded form, the stent wall surface pattern 58 resembles a series of linked S-shapes 22 formed radially about the tube with interconnections 21 between the radial rows of S's 22 with alternating adjacent S's. Longitudinally, the un-expanded stent resembles longitudinal rows of pattern series of an S 24, S 24, reverse S 26, reverse S 26 shapes. This series repeats itself along the longitudinal surface of the stent. The longitudinal pattern is interconnected by the radial S's 21. When expanded for implantation within a lumen wall, the stent 20 unfolds to wall surface pattern 60 having linked parallelograms 52 along its longitudinal axis 40 while radially having alternating connected and disjoined struts forming a pattern similar to a butterfly shape 56, along its radial axis 50. The stent 20 can be non-uniform when expanded to accommodate the unique size and shape of the lumen into which it is implanted. The narrow outside diameter of the un-expanded stent eliminates the usual preliminary lumen expansion step. A multi-layer stent 70 is also provided. A method of implantation and a method of manufacture are also provided.

18 Claims, 14 Drawing Sheets

*Fig. 9*
Plastic Strain Vs Diameter
DIRECT-STENT Coronary Stent

INTRA VASCULAR STENT

FIELD OF THE INVENTION

This application is filed under 35 U.S.C. 111 (a) claiming priority of a provisional patent application No. 60/157,822 filed under 35 U.S.C. 111(b), filed Oct. 5, 1999.

The present invention relates to a radially expandable intra vascular stent for use as a tubular structure that may be left within a body lumen, such as within a coronary artery, to maintain the patency of the body lumen. The present invention particularly relates to a stent that includes a flexible tubular body having a relatively high percentage of metal, in relation to open space, a narrow cross-section for ease of insertion and a surface pattern that permits expansion of the stent in a uniform or a non-uniform manner as needed to accommodate the size, shape and position of the lumen being stented.

BACKGROUND OF THE INVENTION

Angioplasty is used to increase the lumen diameter of an artery where the artery has become narrowed, or stenosed, for a variety of reasons. Balloon angioplasty has been successfully used in the placement of stents to permanently enlarge such a stenosis, especially in coronary arteries. Numerous coronary stents have been provided in the prior art that are adapted to provide a uniform expansion of the stent in a lumen wall. One example of a type of prior art include stents formed of wire wound around a mandrel. Another type of prior art includes stents formed of thin-walled metal tubes cut to permit compression for delivery . These prior art tubular stents have limited longitudinal stability when expanded. Both of these types of prior art stents require a preliminary step to expand the diameter of the lumen to be stented. These stents also, when implanted, expand to a uniform diameter without regard to the twists and turns of the lumen wall.

While these stents may be suitable for the particular purpose to which they address, they would not be as suitable for the purposes of the present invention as hereafter described. Therefore, a need exists for a stent that provides longitudinal flexibility in combination with increased hoop strength, torsional stability, longitudinal stability and radial flexibility. The stent of the present invention provides these attributes by being formed of a relatively high percentage of metal material providing a high hoop strength to the stent while the stent wall surface pattern delivers a high degree of flexibility while permitting a small amount of longitudinal foreshortening. The stent of the present invention can be applied in a one-step process eliminating the need for a preliminary step dilating the lumen into which the stent is to be placed. It should be noted that the invention is not limited to the applications mentioned which must be considered as solely exemplifying.

SUMMARY OF THE INVENTION

It is an object of the present invention to provide a stent for use in human blood vessels, primarily coronary arteries.

It is a further object of the present invention to provide a stent having the flexibility to present a small cross-section for ease of positioning for implantation while being radially expandable for implantation with a relatively high "hoop" strength as a result of a relatively high percent metal stent surface providing a relatively large metal surface area to free space ratio.

It is an object of the present invention to provide a radially expandible stent with a unique stent wall surface pattern.

I it is an object of the present invention to provide a stent having a relatively small diameter eliminating the need for the preliminary step of expanding the lumen into which the stent is to be placed.

It is a further object of the present invention to provide a stent with minimal longitudinal foreshortening upon expansion in situ.

It is a further object of the present invention to provide a stent with the flexibility to be placed in a curved, narrow lumen in combination with the ability to be expanded in a non-uniform manner to fit the particular lumen size and shape.

The present invention is directed to a stent that satisfies these needs to provide both flexibility and strength in a radially expandable stent. Both are provided as a result of a relatively large metallic surface area, compared to free space, and because of the unique stent wall surface pattern. The un-expended stent has a small cross-section, for case of implantation with balloon angioplasty, and yet offers, increased hoop strength when expanded at the time it is implanted or embedded into the lumen wall. In the un-expanded form immediately after laser cutting, the surface wall pattern resembles a series of continuous S-shapes formed radially about the tube with interconnections between the radial rows of S's with alternating adjacent S's. Longitudinally, the un-expanded stent resembles longitudinal rows of pattern series of an S, S, reverse S, reverse S shapes. This series repeats itself along the longitudinal surface of the stent. The longitudinal pattern is interconnected by the radial S's. In the expanded form, the stent wall surface pattern resembles a connected line of parallelograms along its longitudinal axis while interconnected radially to diamond shapes with alternating connected and disjointed struts form a pattern similar to a butterfly shape, along its radial axis. Because the stent of the present invention is so flexible, the stent can be used in a variety of vessel sizes for repair of fistula, lesions, stenosises, and aneurism . Because a relatively high percentage of metal is used in the present invention, as compared to prior stents, the pattern of the stent delivers a very high hoop strength that is required to prevent re-stenosis. It is planned that the stent will not routinely be expanded to its maximum size. This enables the stent to be formed to fit the lumen into which it is implanted, be it twisted, curved or the like. The expanded outside edges of the stent are, upon expansion of the stent, received into the lumen wall preventing formation of blood clots at the site of the stent.

Another aspect of the stent provides an alternative embodiment with a multi-layer stent that further increases the metal surface area increasing the radial hoop strength of the stent without sacrificing flexibility.

Another aspect of the stent provides a method of implantation of the stent wherein the stent is crimped onto the balloon for balloon angioplasty placement without the preliminary lumen expansion step.

Another aspect of the stent of the present invention also provides a method of manufacturing such a stent.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

Understanding of the invention will be enhanced by referring to the accompanying drawings, in which like numbers refer to like parts in the several views and in which.

DETAILED DESCRIPTION OF THE CURRENTLY PREFERRED EMBODIMENTS

Understanding of the invention will be further enhanced by referring to the following illustrative but non-limiting example.

A stent having features of the present invention comprises a support structure for holding open a lumen within a body, particularly in a coronary blood vessel although the stent of this invention could be used in any size lumen, even a large lumen, such as the esophagus, as a result of fistula, lesion or stenosis. The stent of the present invention has a tubular-shaped body formed from a single metal tube extending along a longitudinal axis having a first end and a second end at opposite ends of the longitudinal axis. The tubular shaped stent body is laser cut to the unique wall surface pattern described herein.

The present invention provides a radially expandable stent having both increased flexibility, providing an expandable stent having a small cross-section for ease of implantation with balloon angioplasty, and yet offers a relatively large metallic surface area as compared to free space, increasing the hoop strength, when opened to be implanted. The stent of this invention is flexible because when the stent is expanded and the surface pattern opens up, the metal stent is in the shape of a series of parallelograms along its longitudinal axis with alternating diamond shapes with connected and disjointed struts forming a pattern similar to a butterfly shape, along its radial axis. The stent can provide increased strength and flexibility yet be implantable in a variety of vessel shapes and sizes. Although the stent is intended for use in coronary arteries, it could be used in any body lumen such as i.e. the esophagus, and any artery in the case of aneurysm The stent of the present invention functions even where not fully expanded, e.g. when a non-uniform stent expansion is required to accommodate a curved vessel. Because a relatively high percentage of metal is used in the present invention, as compared to prior stents, tile surface pattern of the stent delivers a very high hoop strength that is required to prevent re-stenosis.

An alternative embodiment provides a multi-layer stent that further increases the metal surface area increasing the radial hoop strength of the stent.

The present invention also presents a new method of insertion and implantation of such a stent.

The present invention also provides a method of manufacturing such a stent.

Figure 1:
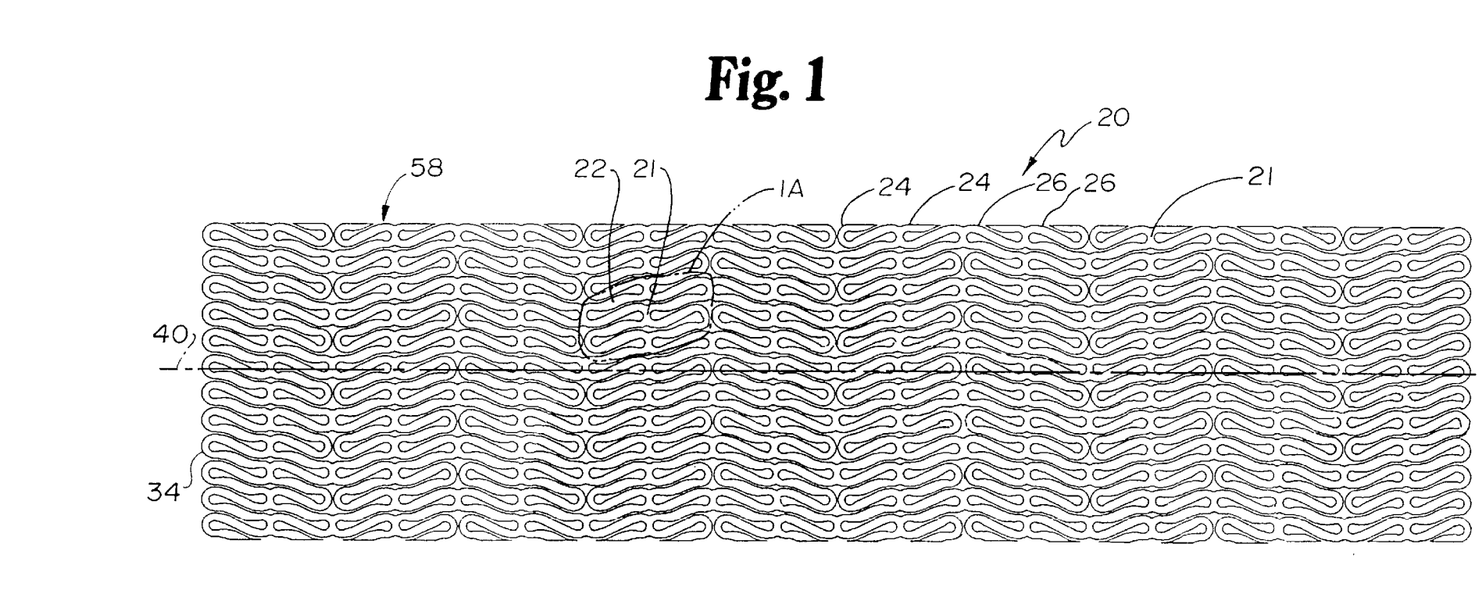
FIG. 1 illustrates the surface of the stent as it appears after being laser cut from a solid metal tube if cut longitudinally and then flattened to a two-dimensional figure.

Turning now to the drawings, in which like reference characters refer to corresponding elements throughout the several views, FIG. 1 illustrates the stent 20 as it appears if cut longitudinally and then flattened to a two-dimensional figure after being laser cut from a solid metal tube, not shown. The stent 20 could be cut from flat sheet metal. The stent 20 is then processed as detailed in FIGS. 3A–3C resulting in a similar stent wall pattern as described herein for the tubular stent of the present invention. This flat stent 20 is then rolled prior for implantation either with a balloon angioplasty or, depending on the material used, self-expanding as is nickel titanium, at the needed site for implantation.

Figure 1A:
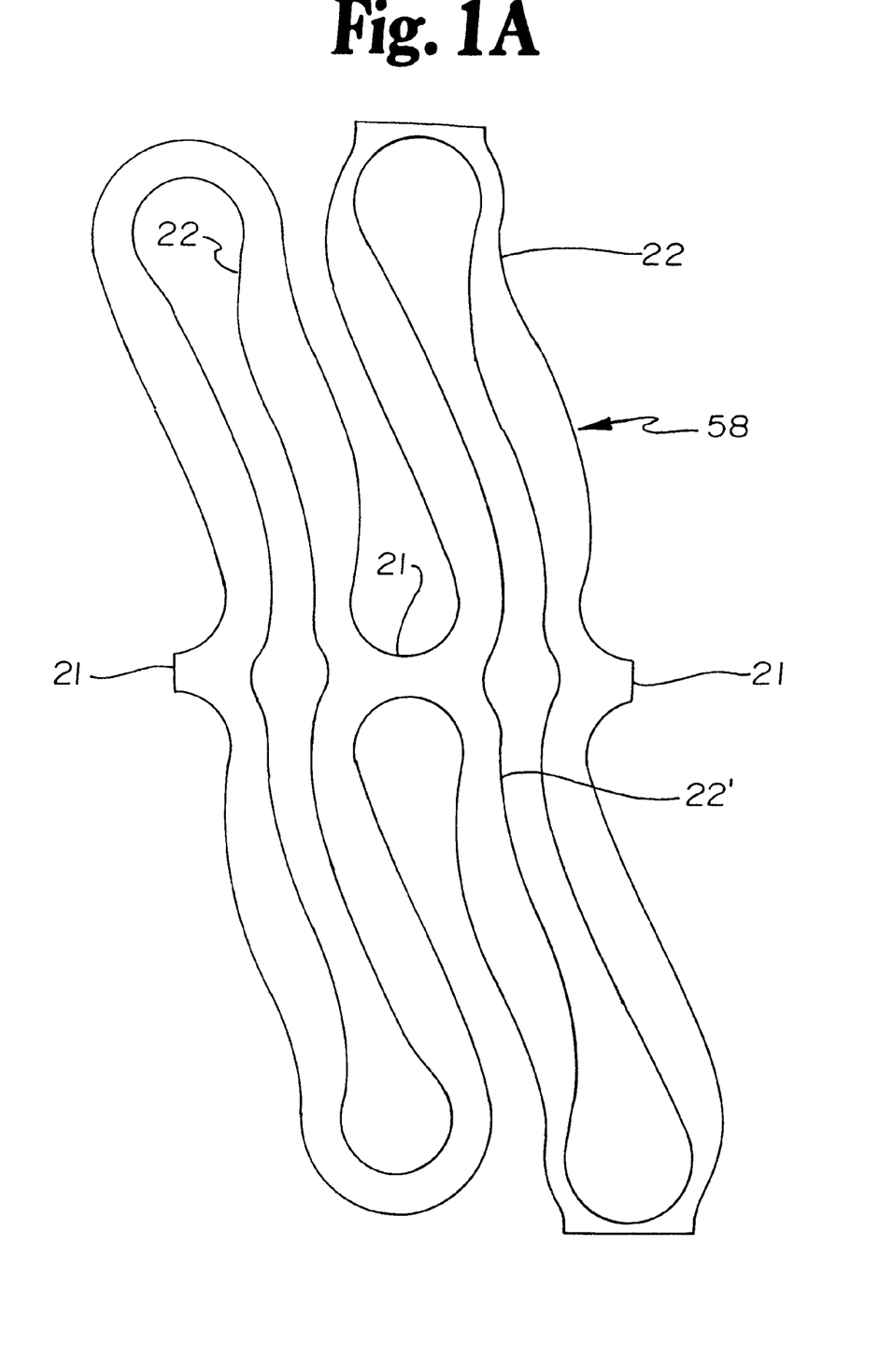
FIG. 1A is an enlarged view of a portion of the stent of FIG. 1.
Figure 2:
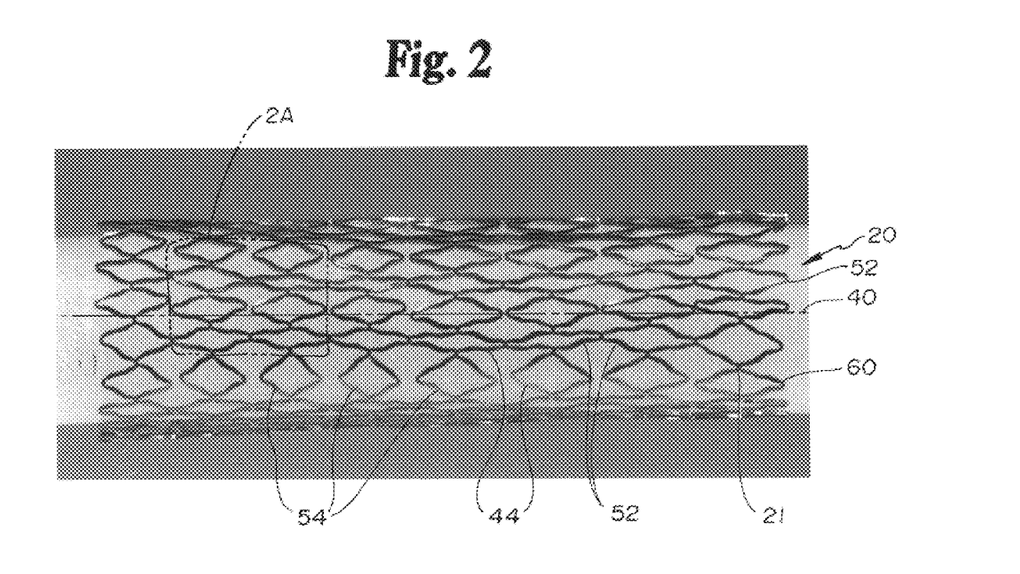
FIG. 2 is a photograph of the stent device of this invention as it appears after implantation.
Figure 2A:
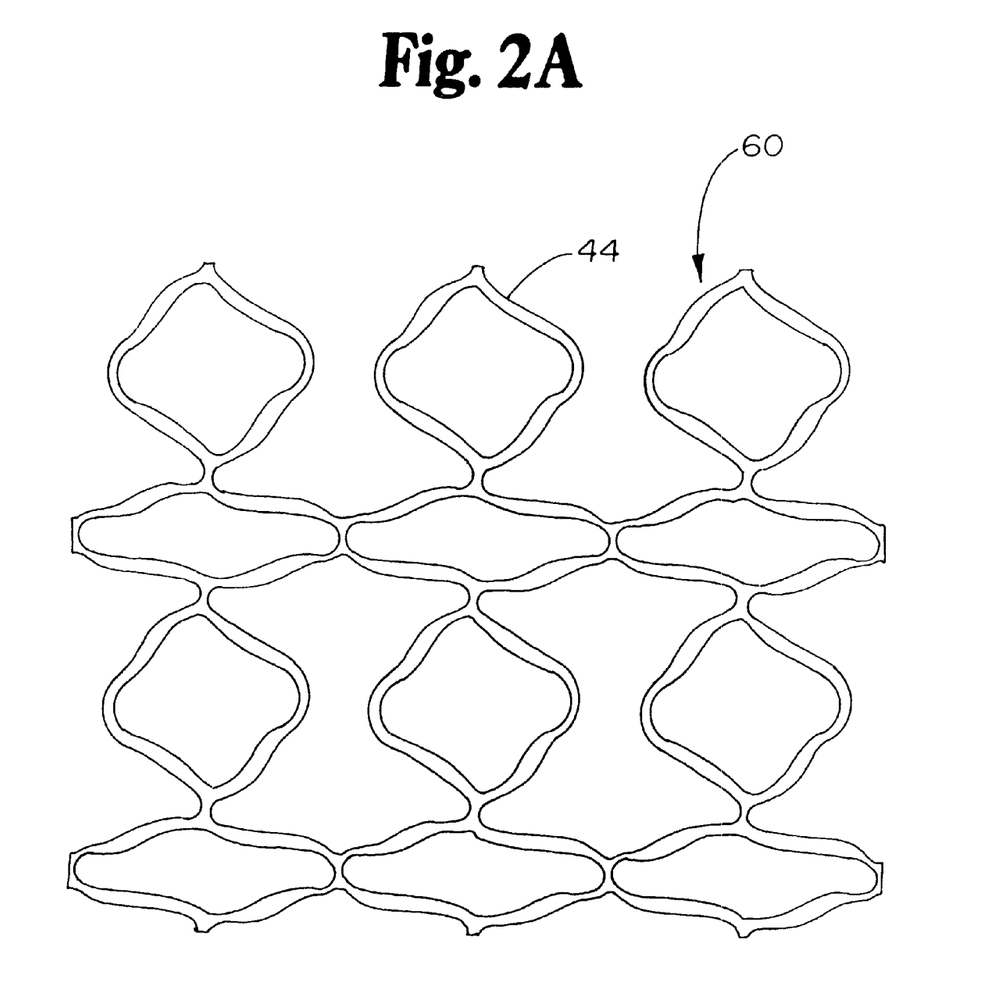
FIG. 2A is an enlarged view of a portion of the stent of FIG. 2.

The longitudinal axis is shown at 40. In the un-expanded form immediately after laser cutting, the surface pattern 58 resembles a series of continuous S-shapes 22 formed radially about the stent 20 with interconnections 21 between the radial rows of S's with alternating adjacent S's, shown in detail in FIG. 1A. An adjacent radial row of S- shapes is indicated at 22. Longitudinally, the un-expanded stent resembles longitudinal rows of pattern series of an S 24, S 24, reverse S 26, reverse S 26 shapes. This series repeats itself along the longitudinal surface of the stent 20. The longitudinal pattern is interconnected by the radial S interconnections 21. Stent 20 is of metal. In actual use, stainless steel, with optional gold plating, has been used although other metals such as titanium, nickel titanium, and tantlun could be used. Any rigid metal could be used. Nickel titanium is a shape memory alloy and can be programmed to self-expand in a vessel. It may also be used without performing balloon angioplasty. Gold plating the stainless steel metal makes the surface smoother and increases the biocompatibility of the stent surface 20. Gold plating also increases radiopacity of the stent 20 making the stent 20 easier to see with radiography during implantation, again helping in placement of the stent 20 within the lumen. Also, the gold plating smooths the inner surface of the stert 20 which aids in maintaining homeostasis by preventing clotting at the site of the stent 20 implantation. In the present invention, the ratio of metal stent surface to free space is increased over that used in the prior art. The metal percentage in the present invention is in the range of 20–30 percent although 22 percent has been determined to be the optimal amount for coronary arteries. The stent 20 of this invention is referred to as a direct stent because no preliminary step to enlarge the lumen is required. This higher percentage of metal surface provides a higher radial or hoop strength to the stent 20 as compared to prior art stents. FIG. 2 indicates the plastic strain showing when the material experiences fatigue and no longer has the strength properties. Stainless steel (316L) was found to break at 35% strain. As a result, the stent 20 of the present invention is expected to a point of the strain of loss than 25%, well below the level of material fatigue.

FIG. 2 illustrates the expanded stent 20 as it appears after processing and at implantation. The expanded stent 20 includes a generally tubular body having a first end 16 and a second end 18 at opposite ends of the longitudinal axis 14. Stent 20 is in the shape of a series of parallelograms along its longitudinal axis 14 and alternate radial rows of interconnected generally diamond shapes 54 interconnecting with said longitudinal rows of interconnected generally parallelogram shapes forming butterfly shaped spaces there between. The stent in FIG. 2 is ready for balloon angioplasty placement of the stent 20 into a lumen without pre-dilation of the lumen. The particular pattern of the stent 20 enables it to be place in a variety of settings. The relatively high percentage of metal provides strength while the open areas of the stent 20 make the stent 20 very flexible in what lumen sizes, shapes it can to which it can be placed and to which it conforms. The stent 20 can accommodate curved vessels, and vessel of different sizes and shapes. The stent 20 provides strength where needed to prevent re-stenosis in a selected area of a lumen.

The particular expanded wall surface pattern 60 in the stent 20 can accommodate expansion to an outside diameter size of 5 mm. The stent 20 is implanted into the lumen wall by expansion of the stent 20 at the selected site within the lumen by the expansion of the balloon. The stent 20 can open up to provide high hoop strength throughout its length even while expanded non-uniformly. The stent 20 conforms to the body vessel rather than the vessel conforming to the stent shape as in the prior art. Stent 20 diameters could be increased beyond 5 mm, even to 10 mm, although not for use in coronary arteries.

Figure 3:
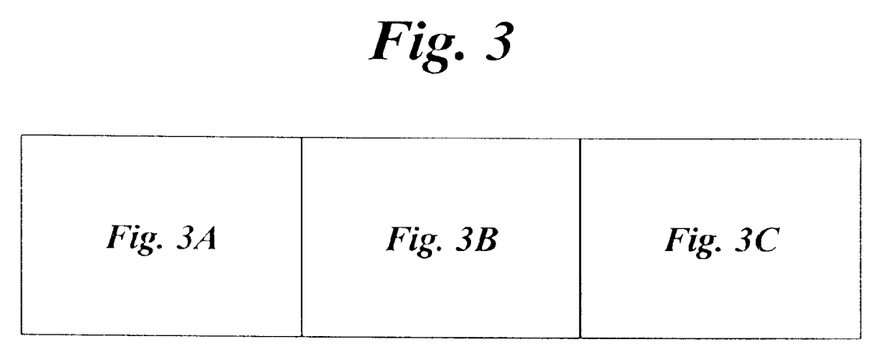
FIG. 3 is a chart combining the flow charts of FIGS. 3A, 3B, and 3C detailing the method of manufacture of the device of this invention.
Figure 3A:
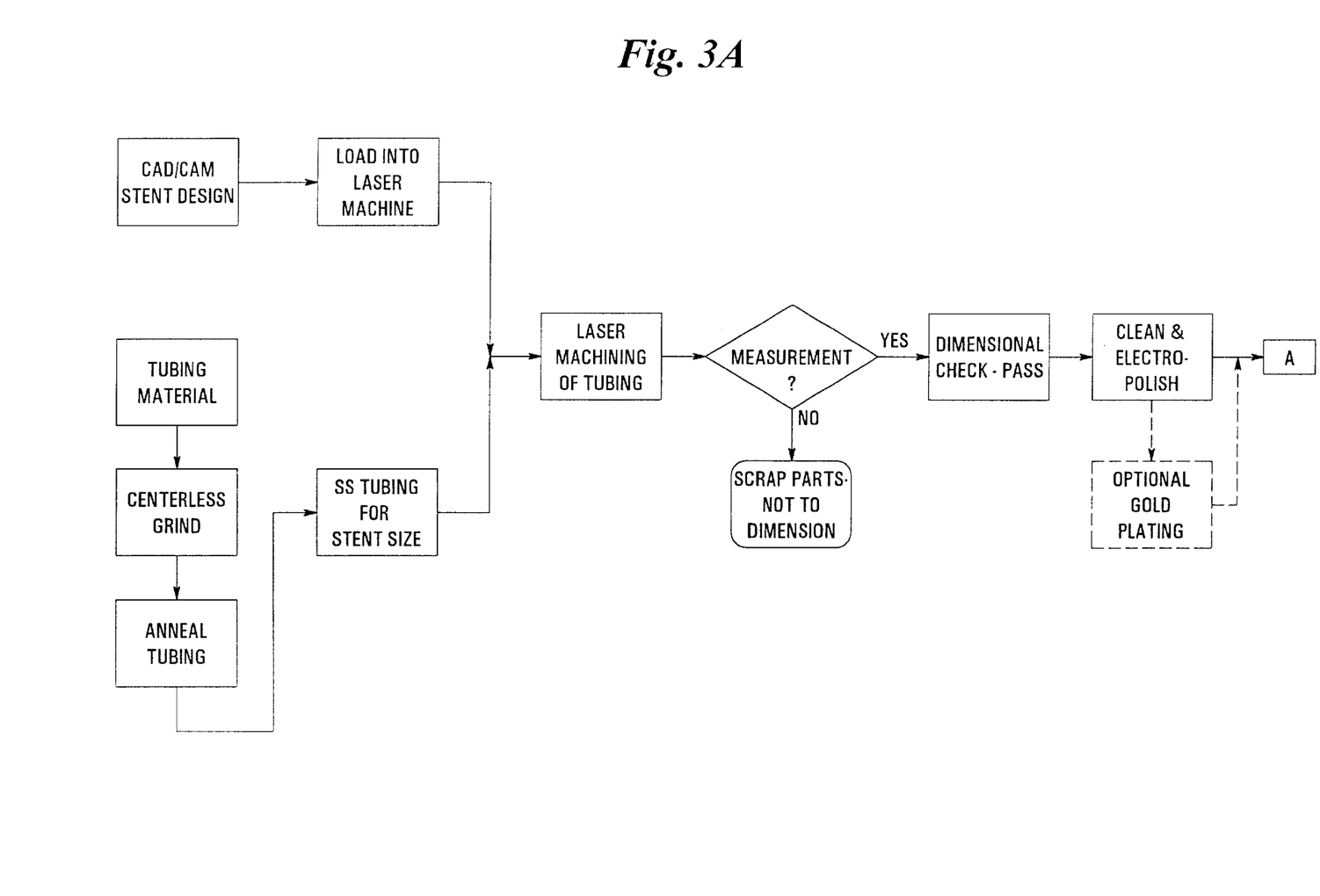
Figure 3B:
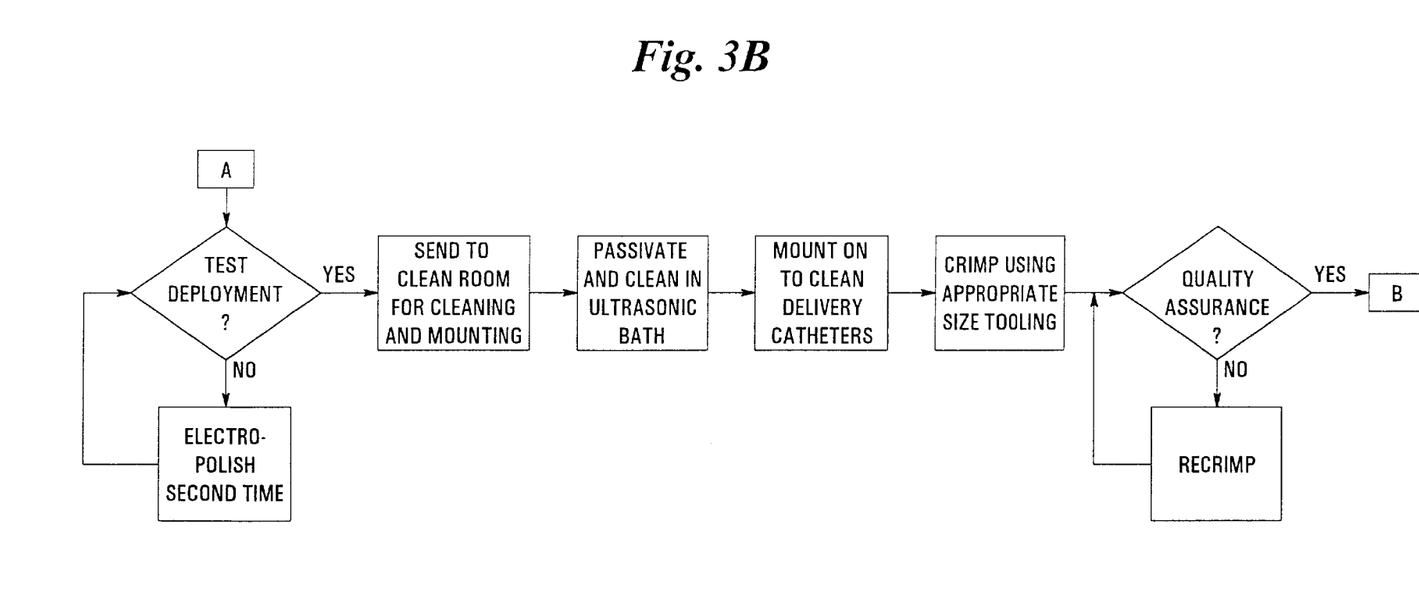
Figure 3C:
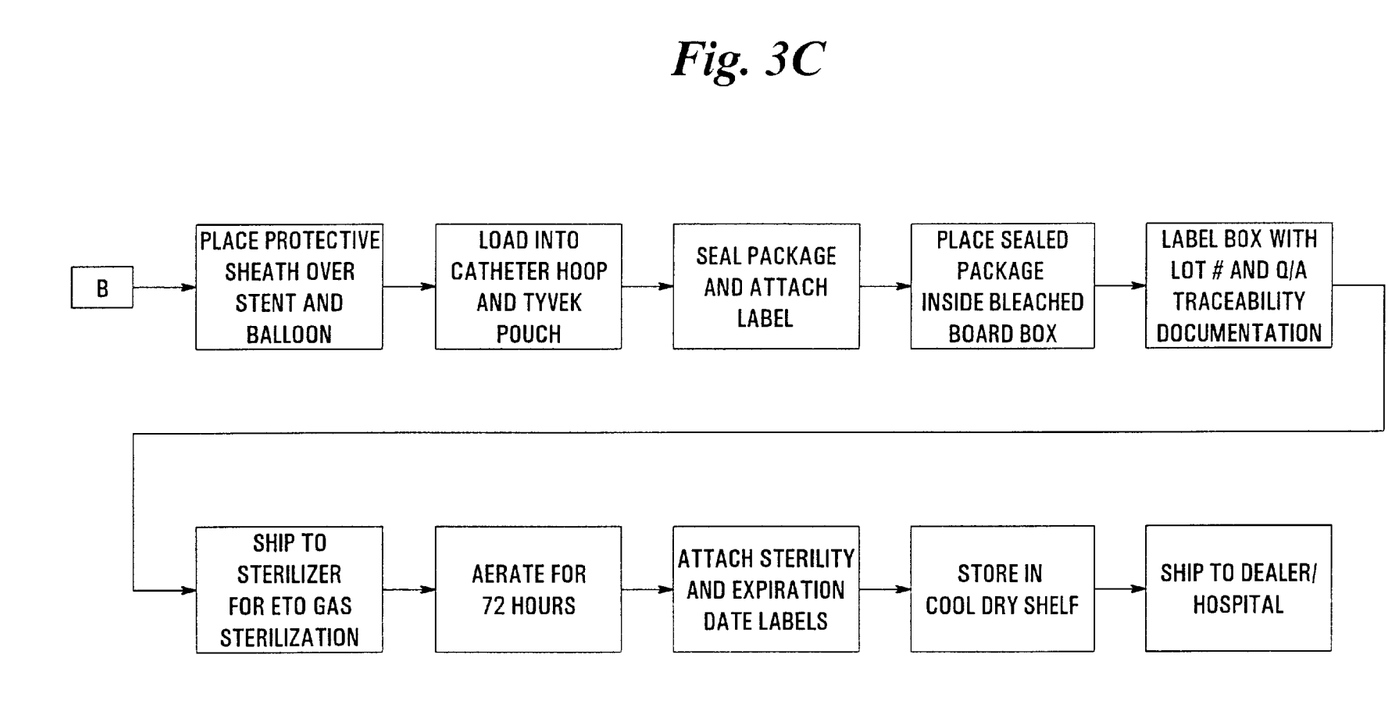

FIG. 3 is a chart combining the flow charts of FIGS. 3A, 3B, and 3C detailing the method of manufacture of the stent 20 of this invention. FIG. 3A details the step by step process taking the stent 20 from its origin as a metal tube to a laser machined stent with optional gold plating. A similar process is used in making the multi-layer stent 70.

Specifically, the stent 20 starts as a solid metal tube that is ground along an outside surface to smooth the tube. This is done by a centerless grinding to both smooth the surface and to size the tube to the selected internal dimension and tube thickness. The tube is next annealed to soften the metal to enable it to be more easily be cut by laser machining. The particular surface design is selected and programmed into a CAD design computer program which is then loaded into the laser machine. The tube is then cut by laser means to the particular stent wall surface pattern 58 of this invention. S-shapes 22 are formed both as rows along the radial axis 50 and in repeated series of S 24, S 24, reverse S 26, reverse S 26, along the longitudinal axis 40, as shown in FIG. 1.

After the tube is laser machined, the tube is cut to the required stent 20 lengths. Quality control inspection occurs at this time weeding the stents of improper length and pattern cut. The stents 20 are then electro-polished and gold plated, if desired.

FIG. 3B continues the process including testing of the stent 20 for smoothness and selecting stents 20 to be re-polished. Once the stent 20 passes inspection, it is sent for sterilization and mounting onto clean delivery balloon catheters for balloon angioplasty. The first stent end 34 and second stent end 36 are crimped to prevent accidental stent 20 placement and to ease threading of the stent 20 through the lumen and eventual placement of the stent 20. The stent 20 is then again inspected to see that the crimping has been done properly.

FIG. 3C continues the process with the clean, inspected catheter-mounted stent 20 is then packaged and labeled and shipped for sterilization and shipped to the hospital for use.

Figure 4:
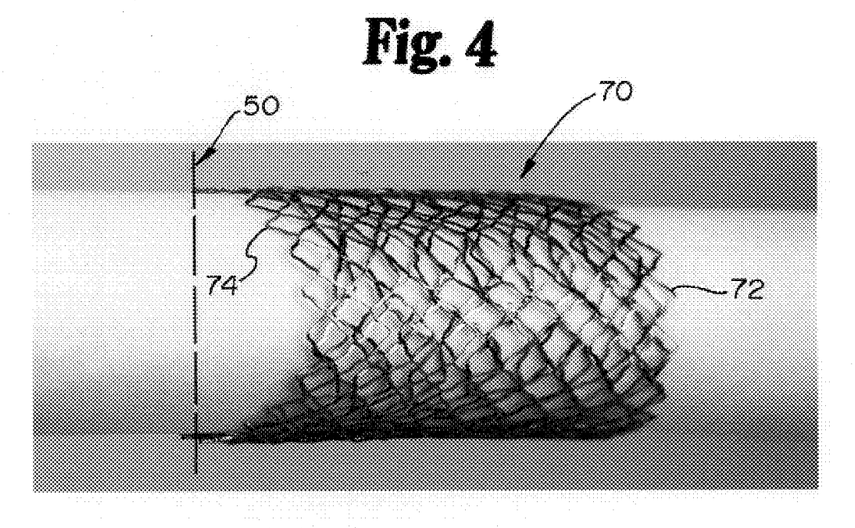
FIG. 4 is a photograph of an alternate embodiment, a multi-layer stent as it appears after implantation, of the device of this invention.

FIG. 4 illustrates an alternate embodiment, a multi-layer stent 70 with an inside stent 72 beneath the surface of the outside stent 74 shown at as it appears after processing and prior to placement. FIG. 4 is a photograph of an actual multi-layer stent 70 ready for placement. The particular expanded wall surface pattern 60 of the present invention is shown. Having a stent 72 within a stent 74 further increases the metal surface area of the multi-layer stent 70. In FIG. 4, a two-layer stent is presented although more layers could be added. Adding layers would increase both the surface area increasing the percentage of metal and thus further strengthening the stent 70 and resulting in a larger outside diameter of the multi-layer stent 70 require a preliminary step to enlarge the lumen prior to placement of the multi-layer stent 70. This multi-layer stent 70 would be especially useful in, ex. fistula, lesions or aneurysm, where more hoop strength is needed and flexibility is less of a concern.

Figure 5:
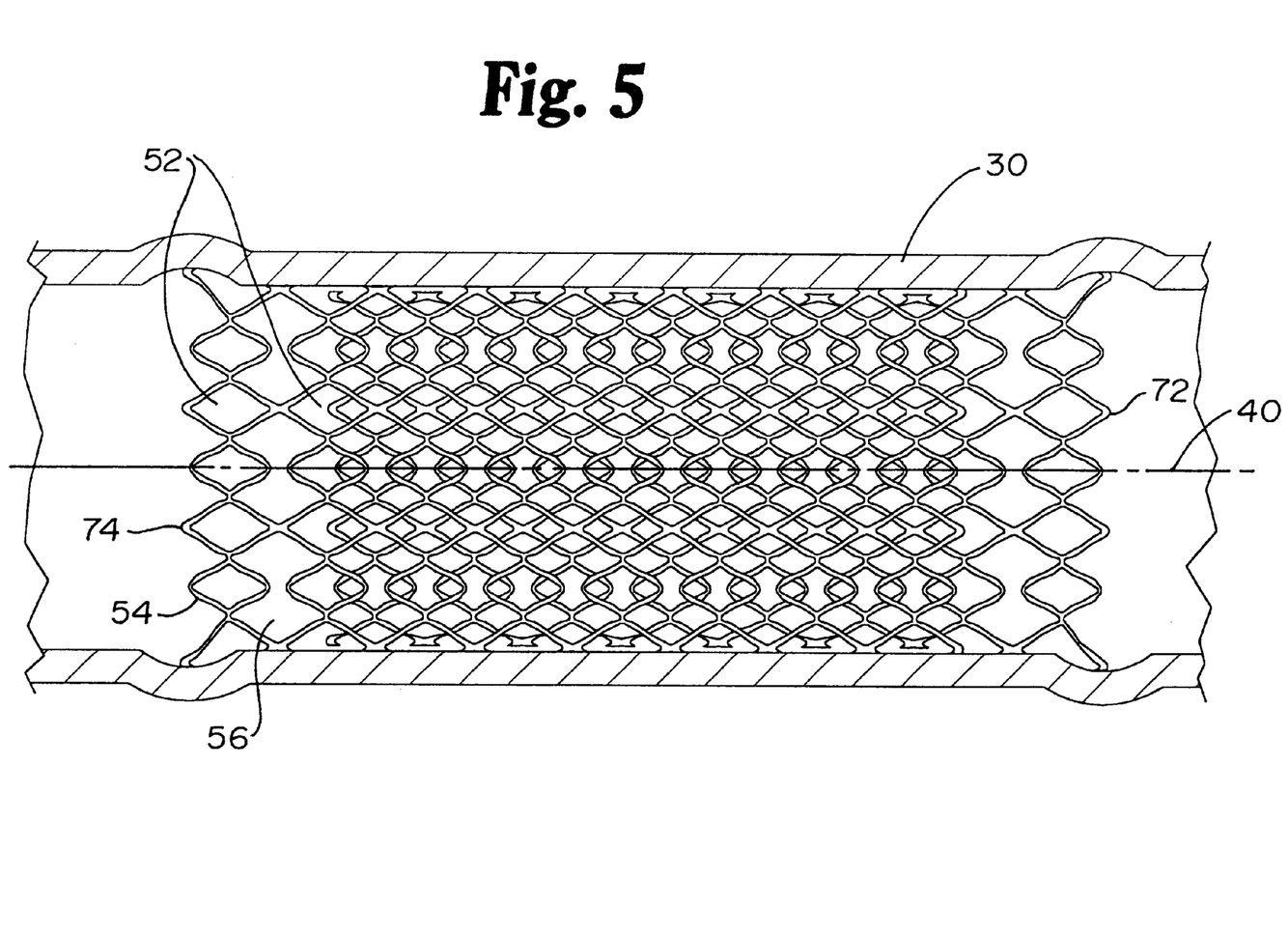
FIG. 5 is a diagrammatic side elevational view of the embodiment of FIG. 4, a multi-layer stent, showing an inside stent beneath the surface of the outside stent, as it appears after implantation.

FIG. 5 is a schematic diagram of the multi-layer stent 70 in its expanded state in its position of use inside a lumen wall 30 with an inside stent 72 beneath the surface of the outside stent 74. In this figure, the stent 70 is shown imbedded in the lumen wall 30 during implantation of the stent 70. This process is the same for the single layer stent 20. For ease in understanding, the multi-layer stent 70 is shown with uniform expansion.

Figure 6:
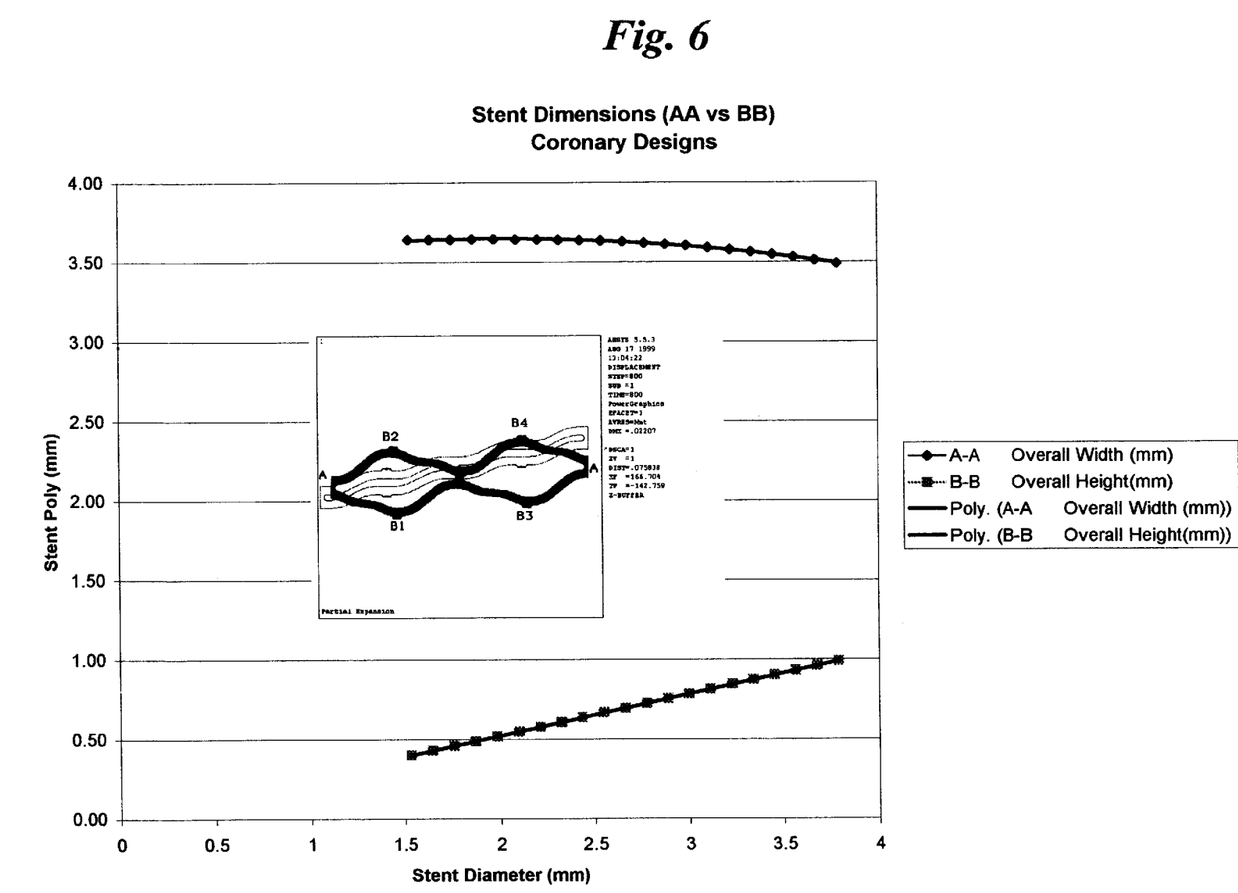
FIG. 6 is a computer generated graph illustrating the small amount of foreshortening, shown at A—A, as the stent of this invention is expanded in diameter as a result of increased size of the diamond shapes B—B, during partial expansion.

FIG. 6 illustrates the small amount of foreshortening of the stent of this invention, A—A, as a result of increased size of the diamond shapes B—B, during partial expansion of the stent 20 device of the present invention. The chart reflects that the stent 20 does not significantly contract in length as the diameter is increased. Even as the diameter in increased to 4 mm, the stent 20 length is still 3.5 mm. The insert within the graph shows the un-expended stent in phantom with the expanded stent imposed thereon.

Figure 7:
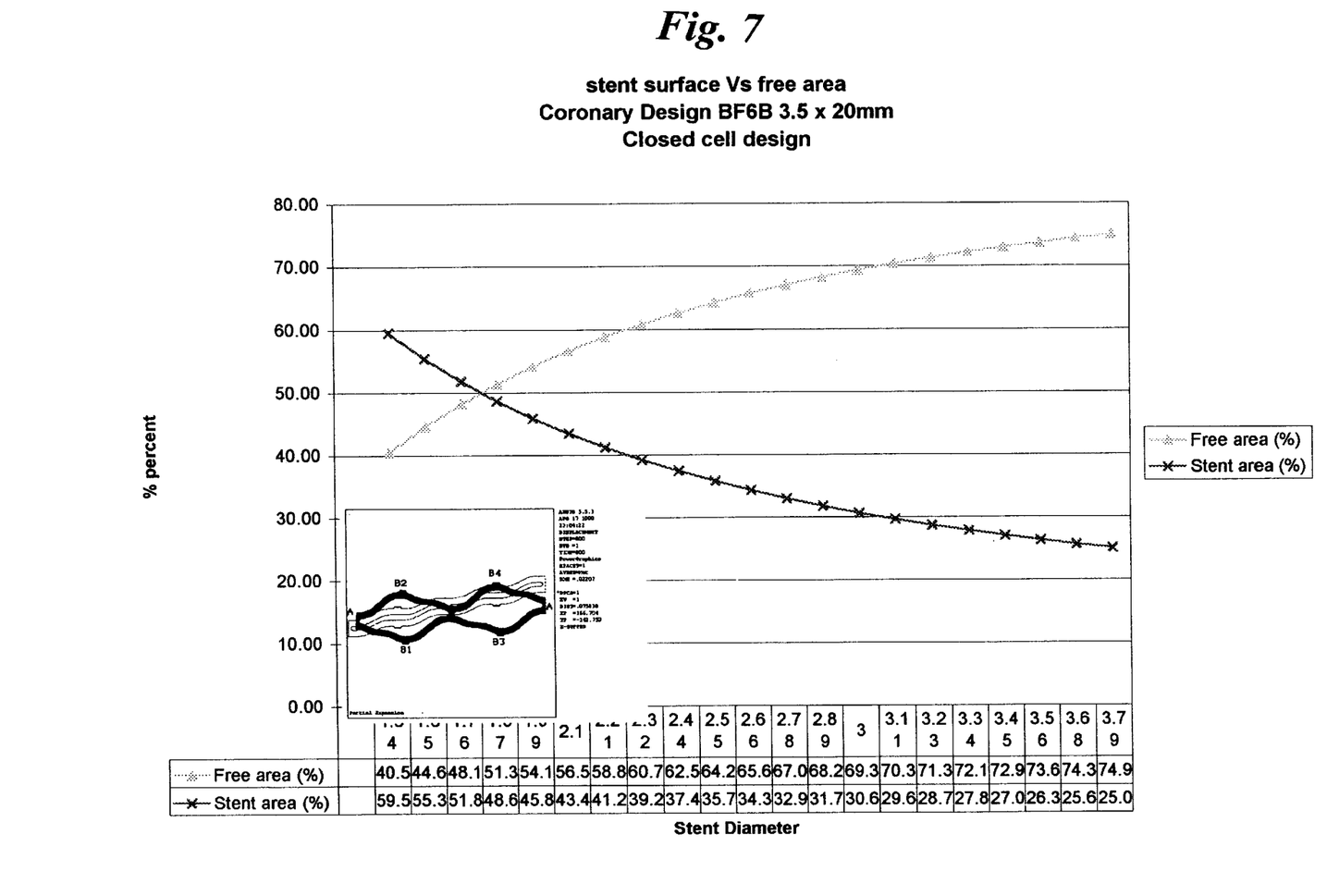
FIG. 7 is a computer generated graph illustrating the stent metallic surface area versus free area as the stent embodiment device of this invention is increased in diameter.

FIG. 7. illustrates the stent surface area versus free space as the stent 20 is increased in diameter. Here the stent 20, a closed cell stent, is expanded, the surface pattern 60 is spread out more and so the amount of free space increases. A larger diameter results in a higher percentage of free space. The insert within the graph shows the un-expended stent in phantom with the expanded stent imposed thereon.

Figure 8:
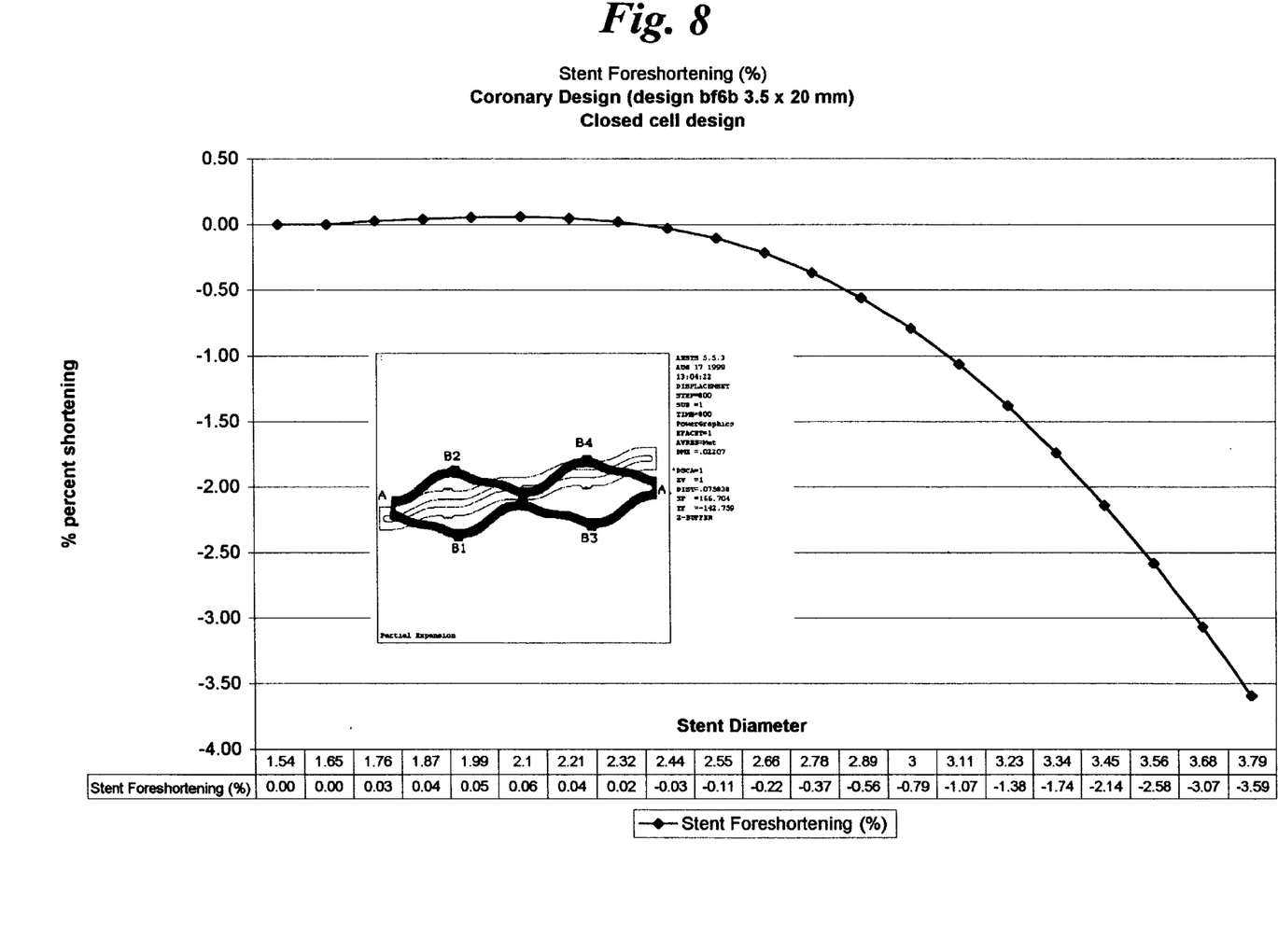
FIG. 8 is a computer generated graph illustrating the percentage of foreshortening of the stent device of the invention as it is increased in diameter upon partial expansion.

FIG. 8 illustrates foreshortening of the stent 20 as the stent 20 is increased in diameter upon partial expansion. This graph follows FIG. 6 with the percentage of foreshortening as the stent is increased in diameter. As illustrated, even as the stent 20 is increased to 3.79 mm in diameter, the percentage of contraction of the stent is less than 4%. The insert within the graph shows the un-expanded stent in phantom with the expanded stent imposed thereon.

Figure 9:
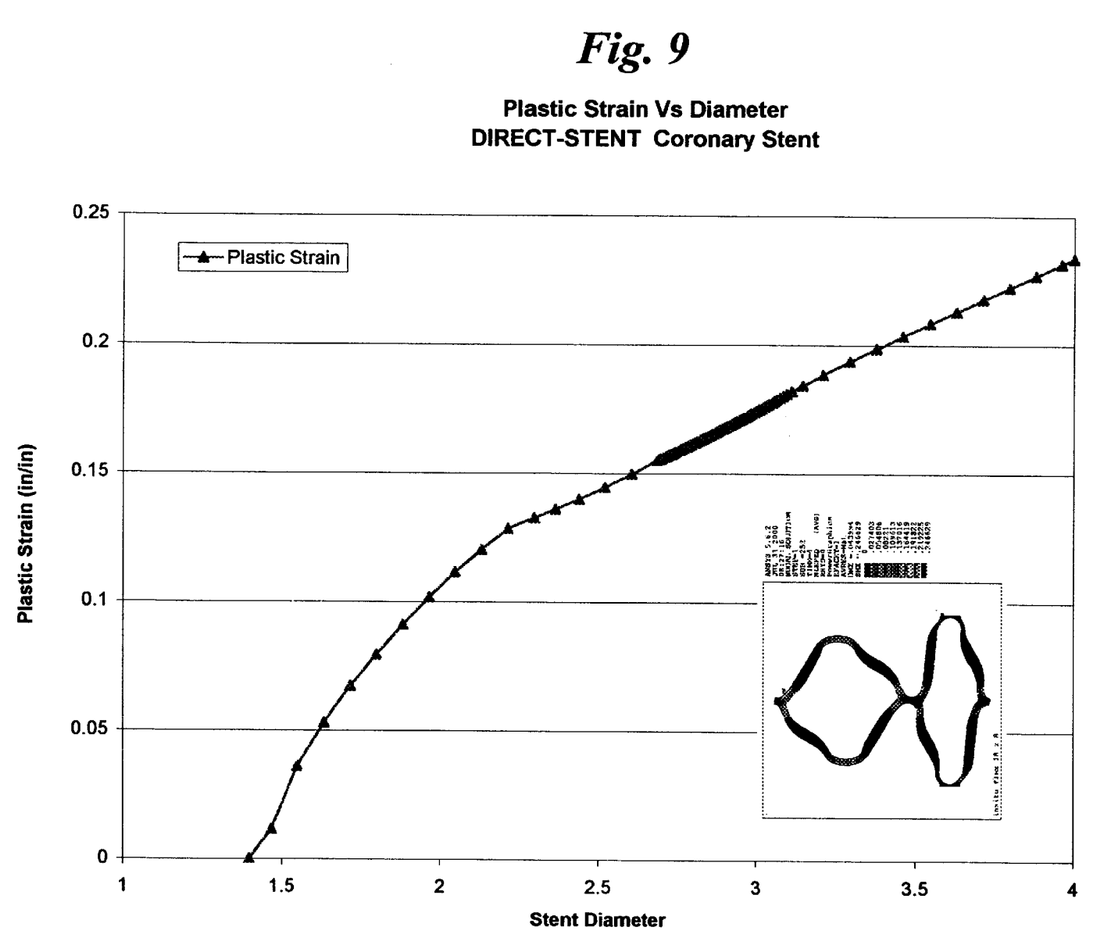
FIG. 9 is a computer generated graph illustrating the increase in plastic strain as the stent device of this invention is increased in diameter.

FIG. 9 shows the plastic strain, the measure of how much strain the material experiences upon expansion as the diameter increases. The maximum plastic strain of the material used in the present invention, stainless steel, without deterioration, is 35%. The strain permitted in the present invention is less than 25%. The insert within the graph shows the un-expanded stent in phantom with the expanded stent imposed thereon.

Although the present invention has been described in considerable detail with reference to certain preferred versions thereof other versions are possible. The stent of the present invention is able to be used in peripheral blood vessels as well as coronary arteries. The stent of the present invention is suitable for implantation in any vessel on the human body that is able to be stented. Therefore, the spirit and scope of the appended claims should not be limited to the description of the preferred versions contained herein.

Changes and modifications in the specifically described embodiments can be carried out without departing from the scope of the invention which is intended to be limited only by the scope of the appended claims.

What is claimed is:

1. A stent for holding open a lumen within a body, particulary in a blood vessel, comprising:
    a) a tubular-shaped stent, formed from a metal tube, extending along a longitudinal axis, having first end and a second end at opposite ends of the longitudinal axis, the stent having a wall surface extending between the first and second ends, the wall surface further comprising an un-expanded wall surface pattern including:
        1) longitude rows of interconnected repeated series of S, S, reverse S, reverse S shapes along the longitudinal axis of said stent;
        2) radial rows of connected S-shapes formed about the outer surface of said tube; and
    b) said wall surface, having a relatively narrow cross-section, providing means for said stent to be placed in the lumen in one step.

2. The stent according to claim 1, wherein said wall surface pattern further provides means for radial expansion of said stent to conform to the size and shape of a lumen wall at implantation.

3. The stent according to claim 2, wherein said wall surface pattern is expanded by means of balloon angioplasty at implantation to embed said stent into the lumen wall.

4. The stent according to claim 3, wherein said expanded wall surface pattern includes:
    a) longitudinal rows of interconnected generally parallelogram shapes; and
    b) alternate radial rows of interconnected generally parallelogram shapes interconnecting with said longitudinal rows of alternately interconnected generally diamond shapes forming butterfly-shaped spaces there between.

5. The stent according to claim 3, wherein said wall surface pattern further provides means for radial expansion of said stent while minimizing foreshortening of said stent at implantation.

6. The stent according to claim 1, said wall surface further comprising a metal surface area in a range between 15 to 30 percent metal as means for providing a high radial force for increasing the hoop strength of said stent.

7. The stent according to claim 1, wherein said stent is of metal of one of the group including stainless steel, nickel titanium, titanium, and tantlun.

8. The stent according to claim 7, further comprising applying a gold plating to said metal of said stent for increasing radiopacity of said stent during placement of said stent enabling said stent to be seen more easily by radiography during implantation of said stent.

9. The stent of claim 8, wherein applying said gold plating further comprises smoothing said stent outer surface and inner surface of said stent decreasing the tendency to clot formation at the site of the implanted stent.

10. The stent according to claim 7, wherein said stent is cut from flat sheet metal and laser cut resulting in a stent surface wall pattern, rolled prior for implantation with a balloon angioplasty.

11. A multi-layer support structure for holding open a lumen within a body, particularly in a blood vessel, comprising:
    a) a first layer stent according to claim 1; and
    b) at least one additional layer stent according to claim 1 adapted to fit over said first layer stent, thereby increasing the percentage metal surface area of said stent for increasing the hoop strength thereof.

12. A method of implantation of the stent according to claim 1, wherein said stent is crimped onto a balloon for balloon angioplasty placement in a single step, said balloon expanding said stent at implantation site forcing said stent into contact with and embedding said stent into the lumen inner wall, said wall surface pattern of said stent providing means for flexibility of radial expansion of said stent even in a non-uniform manner to fit the dimensions of the individual lumen wall.

13. A method of manufacturing the stent according to claim 1, wherein the steps for manufacturing include the following:
    a) providing a solid metal tube, said metal tube selected from a group including stainless steel, titanium, nickel titanium, and tantlum;
    b) grinding said tube outer surface;
    c) heat treating annealing said tube to case laser cutting of said tube outer surface;
    d) cutting said tube to predetermined lengths for formation of a stent;
    e) laser cutting said outer surface of said tube to a predetermined wall surface pattern including connected S-shapes formed in radial rows about the outer surface of said tube and repeated series of S, S, reverse S, reverse S shapes along the longitudinal axis of said stent;
    f) sterilizing said stent;
    g) crimping said stent onto an angioplasty balloon for direct placement of said stent; and
    h) packaging said stent to preserve the sterilized condition of said stent until use.

14. The stent according to claim 1, wherein said wall surface pattern expands non-uniformly in response to radial expansion of said stent by balloon angioplasty to conform the stent to the size, and shape of the lumen wall into which it is implanted.

15. The stent according to claim 14, wherein said wall surface pattern includes:
    a) longitudinal rows of interconnected generally parallelogram shapes, and
    b) alternate radial rows of interconnected generally parallelogram shapes interconnecting with said longitudinal rows of alternately interconnected generally diamond shapes, forming butterfly-shaped spaces there between.

16. The stent of claim 2, wherein said means for radial expansion of said stent to confirm to the size and shape of a lumen wall at implantation further comprises stent wall pattern having S-shapes formed about the outer surface of said tube both longitudinally and radially, said S-shapes of variable widths.

17. The stent of claim 16, wherein said radially expanded stent wall pattern, having S-shapes of variable widths, the expanded outside edges thereof are received into the lumen wall for securing the stent at the desired location and for preventing formation of blood clots at the site of the implanted stent.

18. A stent for holding open a lumen within a body, particularly in a blood vessel, comprising:
   a) a tubular-shaped stent, formed from a metal tube, extending along a longitudinal axis, having a first end and a second end at opposite ends of the longitudinal axis, the stent having a wall surface extending between the first and second ends, the wall surface further comprising an un-expanded wall surface pattern including:
      1) longitudinal rows of interconnected repeated series of S, S, reverse S, reverse S shapes along the longitudinal axis of said stent;
      2) radial rows of connected S-shapes formed about the outer surface of said tube; and
   b) said wall surface having a relatively narrow cross-section for ease of implantation without a preliminary, lumen dilation step; and
   c) said wall surface providing flexibility to said stent for ease of implantation.

\* \* \* \* \*